(12) United States Patent
Gordon

(10) Patent No.: US 8,487,746 B2
(45) Date of Patent: Jul. 16, 2013

(54) JUMP ROPE TRAINING APPARATUS, METHOD, AND SYSTEM

(76) Inventor: Christopher Todd Gordon, Fairfax, VA (US)

( * ) Notice: Subject to any disclaimer, the term of this patent is extended or adjusted under 35 U.S.C. 154(b) by 427 days.

(21) Appl. No.: 12/947,635

(22) Filed: Nov. 16, 2010

(65) Prior Publication Data

US 2011/0115609 A1  May 19, 2011

Related U.S. Application Data

(60) Provisional application No. 61/281,370, filed on Nov. 17, 2009.

(51) Int. Cl.
*H04Q 5/22* (2006.01)
(52) U.S. Cl.
USPC ............................................ 340/10.1; 482/82
(58) Field of Classification Search
USPC ............................................ 310/10.1; 482/3
See application file for complete search history.

(56) References Cited

U.S. PATENT DOCUMENTS

| 6,409,636 | B1* | 6/2002 | Risso et al. | 482/82 |
| 2004/0259689 | A1* | 12/2004 | Wilkins et al. | 482/8 |
| 2006/0189440 | A1* | 8/2006 | Gravagne | 482/8 |
| 2007/0129220 | A1* | 6/2007 | Bardha | 482/82 |
| 2009/0221401 | A1* | 9/2009 | Lovett et al. | 482/3 |
| 2009/0263772 | A1* | 10/2009 | Root et al. | 434/247 |
| 2010/0035688 | A1* | 2/2010 | Picunko | 463/39 |
| 2011/0112861 | A1* | 5/2011 | Hama | 705/2 |

FOREIGN PATENT DOCUMENTS

| WO | 2007/049234 A2 | 5/2007 |
| WO | 2008/062180 A1 | 5/2008 |

OTHER PUBLICATIONS

International Search Report and Written Opinion, dated Jul. 28, 2011, in corresponding International Patent Application No. PCT/US2010/056873, 7 pages.

* cited by examiner

*Primary Examiner* — Brian Zimmerman
*Assistant Examiner* — Omer S Khan
(74) *Attorney, Agent, or Firm* — Maier & Maier PLLC

(57) ABSTRACT

An apparatus, method, and system for jump rope training is disclosed, comprising at least one jump rope, at least one RFID device associated with the at least one jump rope, at least one RFID reader antenna, at least one RFID reader, and at least one coaching device.

6 Claims, 1 Drawing Sheet

JUMP ROPE TRAINING APPARATUS, METHOD, AND SYSTEM

RELATED APPLICATIONS

This application claims priority to U.S. Provisional Application 61/281,370, filed Nov. 17, 2009, and entitled COMPUTERIZED JUMP ROPE TRAINING SYSTEM, the entire contents of which are hereby incorporated by reference.

BACKGROUND

Jump rope training is an extremely effective method of exercise. However, it is difficult for the athlete to monitor his or her performance. The jumper must mentally focus on performing jumps and at the same time stay cognizant of elapsed time, number of jumps, number and duration of rests taken, and an assortment of other information. The jumper must also keep in mind exercise goals such as desired jump rate and desired number of jumps, keep track of any deviation from these goals, and attempt to correct that deviation. This can be overwhelming.

SUMMARY OF THE INVENTION

In one exemplary embodiment, a jump rope training apparatus can be described. The apparatus may include at least one jump rope, at least one Radio-Frequency Identification (RFID) device, at least one RFID reader antenna, at least one RFID reader, and at least one coaching device.

In another exemplary embodiment, a method for jump rope training can be described. The method can include moving an RFID device associated with a jump rope within the antenna footprint of an RFID reader antenna, interpreting the movement of the RFID device as revolutions of the jump rope, monitoring the revolutions of the jump rope, and providing advice based on the revolutions of the jump rope.

In another exemplary embodiment, a jump rope training system can be described. The system can include at least one jump rope, at least one RFID device, at least one RFID reader antenna, at least one RFID reader, and at least one coaching device.

BRIEF DESCRIPTION OF THE FIGURES

Advantages of embodiments of the present invention will be apparent from the following detailed description of the exemplary embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Further, many embodiments are described in terms of sequences of actions to be performed by, for example, elements of a digital control system and the digital signal processing (DSP) devices. It will be recognized that various actions described herein can be performed by specific circuits (e.g., application specific integrated circuits (ASICs)), by program instructions being executed by one or more processors, or by a combination of both. Additionally, these sequences of actions and processes described herein can be considered to be embodied entirely within any form of computer platform having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Figure 1:
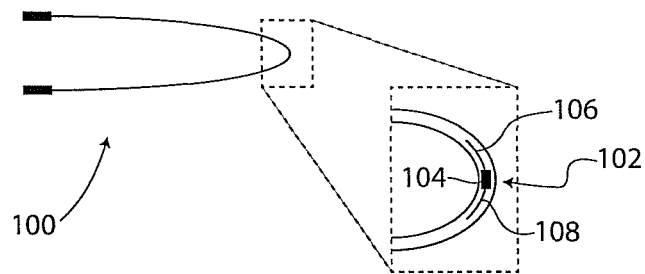
FIG. 1 is an exemplary diagram showing an exemplary embodiment of a jump rope and an RFID device.
Figure 2:
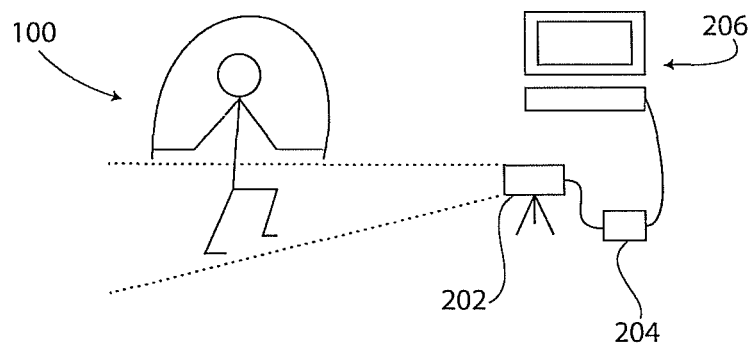
FIG. 2 is an exemplary diagram showing an exemplary embodiment of a jump rope training apparatus.

FIGS. 1-2 generally relate to apparatuses, methods and systems for jump rope training. In exemplary embodiments, the apparatuses, systems, and methods can provide an automated means of monitoring jumper performance by monitoring revolutions of a jump rope. In general, the system can contain a jump rope with an associated RFID device, an RFID reader, and a coaching software application that can monitor jumper performance and provide advice for improvement.

FIG. 1 shows an exemplary embodiment in which an RFID device 102 is associated with a jump rope 100. Jump rope 100 can be a hollow plastic tube approximately one quarter inch in diameter. RFID device 102 can be contained within jump rope 100, and can be anchored at approximately the midpoint by a flexible adhesive. RFID device 102 can also be held in place by the force of the rotation of jump rope 100. In other exemplary embodiments, jump rope 100 can be constructed from any material, for example natural fibers such as leather, hemp, linen, or cotton, or synthetic materials such as nylon, plastic, or cable. Jump rope 100 can be constructed in any configuration, including a solid rope or a hollow tube, and can be of any length and thickness. RFID device 102 can be located inside or outside jump rope 100, and can be attached at any location along the length of jump rope 100 in any fashion.

Still referring to FIG. 1, RFID device 102 can contain an RFID chip 104 and RFID antennas 106 and 108. RFID antennas 106 and 108 can extend any length along jump rope 100 on one or both sides of RFID chip 104, and can be contained inside or outside of the rope. RFID chip 104 can be active or passive. RFID chip 104 can be read-only, or it can be writeable and information can be stored on it. The information stored on RFID chip 104 can be used to identify it's entry into and exit from the antenna footprint of RFID reader antenna 202. In addition, the information stored on RFID chip 104 can include information identifying jump rope 100 itself, information regarding the owner of jump rope 100, and information regarding the owner's top speed, records, past workout history, and training goals, among other things.

Turning to FIG. 2, the revolutions of jump rope 100 can be monitored by an RFID reader antenna 202 and an RFID reader 204. In one exemplary embodiment, reader antenna 202 can be a directed-beam antenna, and can create a shallow planar footprint that can extend to approximately knee level. The footprint can be of any dimensions, for example approximately one to two feet above the floor, with a length of approximately ten feet and a width of approximately 4 feet. Radio-absorbing backdrop materials can be placed opposite reader antenna 202 in order to lessen distortion of the footprint. The user of jump rope 100 can use jump rope 100 within this footprint. As RFID device 102 revolves along with jump rope 100, it can rise up and out of, and then down and into the footprint of reader antenna 202. Each entry/exit pattern can be interpreted as a revolution and therefore a jump.

In another exemplary embodiment, RFID reader antenna 202 can be located in a mat. The footprint created in this embodiment can be of any dimensions, for example approximately two to three feet above the floor, with a length of approximately three feet and a width of approximately four feet. The user of jump rope 100 can use jump rope 100 on this mat and within this footprint. As RFID device 102 revolves along with jump rope 100, it can rise up and out of, and then down and into the footprint of reader antenna 202. Each entry/exit pattern can be interpreted as a revolution and therefore a jump.

In another exemplary embodiment, RFID device 102 can be readable by RFID reader antenna 202 on only one side. RFID device 102 can be affixed to jump rope 100 in such a way that as it revolves along with jump rope 100, the readable side and non-readable side can be presented to RFID reader antenna 202 in a repeating sequence. Each read/non-read pattern can be interpreted as a revolution and therefore a jump.

In another exemplary embodiment, RFID device 102 and RFID reader antenna 202 can make use of a radio frequency that can be blocked by a human body. As RFID device 102 revolves along with jump rope 100, RFID device 102 can be detectable by RFID reader antenna 202 when a human body is blocking it, and undetectable when a human body is not blocking it. Each detection/non-detection pattern can be interpreted as a revolution and therefore a jump.

Still referring to FIG. 2, coaching device 206 can be connected to RFID reader 204. Coaching device 206 can be a personal computer running coaching software. In other exemplary embodiments, coaching device 206 can be implemented using televisions or other visual displays. Coaching device 206 can monitor the performance of the rope as well as provide advice for the user. The coaching software on coaching device 206 can include a monitor component and an advisor component. The monitor component and the advisor component can be run separately or simultaneously, as desired. In some exemplary embodiments, the coaching software can write data to RFID chip 104 in jump rope 100. The coaching software can associate jump rope 100 or other jump ropes with users and store user-specific data. The coaching software can be networked so that multiple jump rope training systems can access data stored on coaching device 206 or on a centralized server. The coaching software can provide informational displays, including graphs, on coaching device 206. The informational displays can be customized as desired. The coaching software can provide visual and audio cues to the user of jump rope 100. The coaching software can be voice activated to indicate certain events, for instance the start and stop of a jumping sequence.

The monitor component of the coaching software that can run on coaching device 206 can track the status of jump rope 100. The monitor component can identify jump rope 100 by reading RFID chip 104, and retrieve, display, and analyze previously stored information associated with jump rope 100. The monitor component can track, display, and record total revolutions. The monitor component can track, display, and record revolutions in revolutions per second and revolutions per minute. If no revolutions of jump rope 100 are detected for a period of time that exceeds a pre-determined time limit, the monitor component can interpret this pause as a rest. The monitor component can track, display, and record the number, relative time, and duration of rests. The monitor component can define intervals as periods of jumping between rests, and workouts as groupings of intervals and rests. The monitor component can track the total time jumping for intervals and for workouts. The monitor component can track, display, and record split times over the course of an interval. The monitor component can interface with a heart rate monitor and track, display, and record heart rates over the course of a workout. The monitor component can calculate calories burned. The monitor component can store all of this information as well as any other information and associate it with jump rope 100 itself or the user of jump rope 100 for future reference.

The advisor component of the coaching software that can run on coaching device 206 can provide advice and analysis for the user of jump rope 100. The advisor component can retrieve and analyze previously stored data associated with jump rope 100 itself or with the user of jump rope 100. The advisor component can use this data to plan subsequent workout sessions. The advisor component can adjust a plan for a workout session during a workout to suit the performance of a user of jump rope 100. The advisor component can plan workout goals according to desired training emphasis. For example, the advisor component could select an aerobic workout which emphasizes cardiovascular fitness, an anaerobic workout which emphasizes quickness and speed, a fat burning workout, or any other type of workout.

The advisor component of the coaching software which can run on coaching device 206 can determine and display a targeted rate of revolutions for jump rope 100. The advisor component can indicate deviations from a targeted rate and guide the user of jump rope 100 in changes in revolution rate toward a targeted rate. The advisor component can also indicate via a countdown when an interval should begin, when a rest should begin, and the amount of time remaining in a workout or an interval. The advisor component can also indicate an amount of revolutions remaining in a workout or interval.

The advisor component can suggest jump techniques for the user of jump rope 100. The advisor component can suggest these jump techniques verbally or through foot diagrams which can be displayed on coaching device 206. The advisor can guide the user of jump rope 100 through pre-workout warm-up exercises and stretches. The advisor component can guide the user through post-workout cool-down exercises and stretches. The advisor component can interface with a heart rate monitor and adjust workout parameters based on the heart rate of the user of jump rope 100. The advisor component can calculate calories burned by the user of jump rope 100 and adjust workout parameters accordingly. The advisor component can include a music playlist of songs suitable for a workout.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method of jump rope training, comprising:
    moving an RFID device associated with a jump rope within the antenna footprint of an RFID reader antenna;
    interpreting the movement of the RFID device as revolutions of the jump rope; monitoring the revolutions of the jump rope; and
    providing advice based on the revolutions of the jump rope, wherein providing advice based on the revolutions of the jump rope further comprises:
    retrieving and analyzing previously stored data associated with the jump rope or with the user of the jump rope;
    planning subsequent workout sessions;
    adjusting a plan for a workout session during a workout to suit the performance of the user of the jump rope;
    planning workout goals according to a desired training emphasis;
    determining and displaying a targeted rate of revolutions for the jump rope;
    indicating deviations from a targeted rate of revolution of the jump rope;
    guiding the user of the jump rope in changes in revolution rate toward a targeted rate;
    indicating when an interval should begin;
    indicating when a rest should begin;
    indicating amount of time remaining in a workout or an interval;
    indicating amount of revolutions remaining in a workout or interval;
    suggesting jump techniques for the user of the jump rope;
    guiding the user of the jump rope through pre-workout warm-up exercise and stretches;
    guiding the user of the jump rope through post-workout cool-down exercises and stretches;
    adjusting workout parameters based on the heart rate of the user of the jump rope;
    calculating calories burned by the user of the jump rope; and
    adjusting a workout based on the amount of calories burned by the user of the jump rope; and playing music suitable for a workout.

2. The method of claim 1, wherein interpreting the movement of the RFID device as revolutions of the jump rope further comprises: noting the entrance of the RFID device into the antenna footprint of the RFID reader antenna; noting the subsequent exit of the RFID device from the antenna footprint of the RFID reader antenna; interpreting this entry and subsequent exit as a revolution of the jump rope.

3. The method of claim 1, wherein interpreting the movement of the RFID device as revolutions of the jump rope further comprises: detecting the readable side of a one-side-readable RFID device within the antenna footprint of the RFID reader antenna; subsequently detecting the non-readable side of a one-side-readable RFID device within the antenna footprint of the RFID reader antenna; and interpreting these detections as a revolution of the jump rope.

4. The method of claim 1, wherein interpreting the movement of the RFID device as revolutions of the jump rope further comprises: operating the RFID device and RFID reader antenna on a frequency that is blocked by the human body; noting when the RFID device is detectable by the RFID reader antenna; noting when the RFD device is subsequently undetectable by the RFID reader antenna; and interpreting detection and subsequent non-detection as a revolution of the jump rope.

5. The method of claim 1, wherein monitoring revolutions of the jump rope further comprises tracking, displaying, or recording least one of: total revolutions per interval; total revolutions per workout; revolutions per second; revolutions per minute; number of rests; relative time of rests; duration of rests; total time jumping per interval; total time jumping per workout; split times over the course of an interval; heart rates over the course of a workout; or calories burned.

6. The method of claim 5, wherein monitoring revolutions of the jump rope further comprises associating the tracked, displayed, or recorded information with the jump rope for future reference.

* * * * *

UNITED STATES PATENT AND TRADEMARK OFFICE
CERTIFICATE OF CORRECTION

PATENT NO. : 8,487,746 B2  
APPLICATION NO. : 12/947635  
DATED : July 16, 2013  
INVENTOR(S) : Gordon Page 1 of 1

It is certified that error appears in the above-identified patent and that said Letters Patent is hereby corrected as shown below:

In the Claims:

Column 6, line 31, should read:

recording at least one of: total revolutions per interval; total

Signed and Sealed this
Twenty-ninth Day of October, 2013

Teresa Stanek Rea
*Deputy Director of the United States Patent and Trademark Office*